(12) United States Patent
Rys et al.

(10) Patent No.: US 11,998,733 B1
(45) Date of Patent: Jun. 4, 2024

(54) SELF-EXPANDING STENT INCLUDING A THIN-FILM NEURAL INTERFACE AND METHOD OF DELIVERING A THIN-FILM NEURAL INTERFACE USING A SELF-EXPANDING STENT

(71) Applicant: Verily Life Sciences LLC, South San Francisco, CA (US)

(72) Inventors: Kenneth Rys, Burlingame, CA (US); Bo Lu, Burlingame, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 233 days.

(21) Appl. No.: 17/385,525

(22) Filed: Jul. 26, 2021

Related U.S. Application Data

(60) Provisional application No. 63/058,833, filed on Jul. 30, 2020.

(51) Int. Cl.
*A61N 1/05* (2006.01)
*A61F 2/89* (2013.01)
*A61N 1/375* (2006.01)

(52) U.S. Cl.
CPC .............. *A61N 1/0558* (2013.01); *A61F 2/89* (2013.01); *A61F 2230/0006* (2013.01); *A61F 2230/0008* (2013.01); *A61N 1/37516* (2017.08)

(58) Field of Classification Search
CPC ........................................................ A61F 2/89
See application file for complete search history.

(56) References Cited

U.S. PATENT DOCUMENTS

| | | | | | |
|---|---|---|---|---|---|
| 5,104,404 | A | * | 4/1992 | Wolff | A61F 2/89 623/1.16 |
| 5,769,887 | A | * | 6/1998 | Brown | A61F 2/958 606/198 |
| 2002/0107563 | A1 | * | 8/2002 | Shanley | A61F 2/915 623/1.15 |
| 2004/0093077 | A1 | * | 5/2004 | White | A61F 2/915 138/119 |
| 2005/0080481 | A1 | * | 4/2005 | Madda | A61F 2/856 623/1.42 |
| 2005/0143801 | A1 | * | 6/2005 | Aboul-Hosn | A61B 17/11 623/1.11 |

(Continued)

*Primary Examiner* — Jacqueline Woznicki
(74) *Attorney, Agent, or Firm* — Kilpatrick Townsend & Stockton LLP

(57) ABSTRACT

The present disclosure relates to a medical device, methods of making a medical device, and methods of delivering medical device. Particularly, aspects of the present disclosure are directed to a medical device having a self-expanding stent and a thin-film neural interface. The stent comprises a plurality of struts having a substantially elliptical or circular geometry arranged in series from a proximal end to a distal end of the stent, and a thin-film neural interface attached to the stent. Each strut of the self-expanding stent comprises a top portion and a base portion integrally connected with the top portion at a first connection point and a second connection point such that the top portion moves relative to the base portion. The self-expanding stent provides a retracted configuration to protect the thin-film neural interface during delivery, and an expanded configuration to deploy the thin-film neural interface.

13 Claims, 10 Drawing Sheets

(56) References Cited

U.S. PATENT DOCUMENTS

| | | | | |
|---|---|---|---|---|
| 2006/0111772 A1* | 5/2006 | White | ...................... | A61F 2/844 |
| | | | | 623/1.15 |
| 2017/0036012 A1* | 2/2017 | Tabada | ..................... | A61B 5/24 |
| 2018/0153689 A1* | 6/2018 | Maimon | ............... | A61F 2/2418 |
| 2018/0333571 A1* | 11/2018 | Pepin | ................... | A61N 1/0556 |
| 2018/0344456 A1* | 12/2018 | Barash | .................. | A61F 2/2418 |
| 2020/0155857 A1* | 5/2020 | Lu | ........................... | H05K 1/115 |
| 2022/0212016 A1* | 7/2022 | Yaffe | ..................... | H01B 3/305 |
| 2022/0347470 A1* | 11/2022 | Lai | ....................... | A61N 1/3616 |
| 2023/0172732 A1* | 6/2023 | Karicherla | ........... | A61N 1/0551 |
| | | | | 623/1.11 |

* cited by examiner

SELF-EXPANDING STENT INCLUDING A THIN-FILM NEURAL INTERFACE AND METHOD OF DELIVERING A THIN-FILM NEURAL INTERFACE USING A SELF-EXPANDING STENT

CROSS-REFERENCE TO RELATED APPLICATIONS

This application claims priority to and the benefit of U.S. Provisional Application No. 63/058,833, filed Jul. 30, 2020, which is incorporated herein by reference in its entirety
FIELD The present disclosure relates to self-expanding stents, and in particular to self-expanding stents including a thin-film neural interface, methods of making self-expanding stents including a thin-film neural interface, and methods of delivering a thin-film neural interface using a self-expanding stent.

BACKGROUND

Normal neural activity is an intricate balance of electrical and chemical signals, which can be disrupted by a variety of causes (genetic, chemical or physical trauma) that affect the nervous system, causing cognitive, motor and sensory impairments. The ability to monitor brain electrical and chemical activity in real time and with noninvasive or minimally invasive techniques is important for both the understanding of nervous system functioning in health and disease and the development of effective treatment options for those disorders. Moreover, the ability to restore the diseased nervous system to an intact and normal-functioning state or substitute lost function with brain-actuated assistive devices is dependent on techniques to translate that monitoring information into effective treatment modalities, e.g., to stimulate brain tissue and modulate brain activity. One example of neuroprosthesis/brain-machine interface (BMI) and neuromodulation technology, deep brain stimulation (DBS), has proven to be effective for treatment of essential tremor disorder, Parkinson's disease, dystonia, epilepsy and psychiatric disorders such as depression, obsessive compulsive disorder and Tourette syndrome. Another example of neuroprosthesis/BMI and neuromodulation technology, brain-computer interfacing (BCI), translates specific features of signals recorded from the brain into outputs that allow the user to act on the world without the participation of peripheral nerves and muscles and has proven effective for motor rehabilitation following stroke, Parkinson's disease, and psychiatric disorders.

Neuroprosthesis/BMI and neuromodulation devices and systems typically comprise an implantable, semi-implantable or external processing unit (e.g., a neurostimulator with a pulse generator, a processor with signal recorder, or the like) having electronics connected to a lead assembly that can deliver electrical pulses to or record signals from electrodes interfaced with nerves or nerve bundles via a neural interface. In conventional neuroprosthesis/BMI and neuromodulation technology, a recurring issue is that electronics (e.g., electronics connected to a lead assembly that can deliver electrical pulses to or record signals from electrodes interfaced with nerves or nerve bundles via a neural interface) are frequently damaged during delivery to a target biological structure. For example, a high-density electrode is subjected to high stresses and/or strains when delivered to a target biological structure due to, for example, narrow vascular canals. The high stresses and/or strains on the electrodes can result in damage to the electrodes or the electrodes can be dislodged from the neural interface. Thus, it would be desirable to identify devices and techniques for delivering electronics to a target biological structure without damaging the electrodes.

SUMMARY

In various embodiments, a medical device is provided that comprises: a stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion; a first cross-bar attached to the first connection point of each strut of the plurality of struts; a second cross-bar attached to the second connection point of each strut of the plurality of struts; and a third cross-bar attached to the top portion of each strut of the plurality of struts; and a thin-film neural interface comprising: a supporting structure having a first surface and a second surface opposite of the first surface; and one or more electrodes formed on the first surface of the supporting structure, wherein the second surface of the supporting structure is attached to the bottom portion of each strut of the plurality of struts.

In some embodiments, the first hinge and the second hinge allow the top portion to move at an angle relative to the base portion, and wherein the angle ranges from −30° to 90°. I In some embodiments, each strut of the plurality of struts have an elliptical or circular geometry.

In some embodiments, the base portion of each strut of the plurality of struts is an arc that is less than one half of a circumference of the elliptical or circular geometry, and wherein the top portion of each strut of the plurality of struts is an arc that is greater than one half of a circumference of the elliptical or circular geometry.

In some embodiments, the stent is formed of a shape-memory material, and wherein the shape-memory material comprises stainless steel, Nitinol, nickel, titanium, or any combinations thereof.

In some embodiments, the stent is a monolithic structure.

In some embodiments, each strut of the plurality of struts is spaced a predetermined distance from adjacent struts of the plurality of struts.

In some embodiments, the predetermined distance is at least 0.5 mm.

In some embodiments, the thin-film neural interface further comprises a wiring layer formed on the supporting structure, and the one or more electrodes are electrically connected to the wiring layer, and wherein the supporting structure comprises one or more layers of dielectric material.

In some embodiments, the dielectric material is liquid crystal polymer.

In some embodiments, the medical device further comprises: a cable comprising: the supporting structure comprised of the dielectric material; one or more conductive traces formed on the supporting structure and electrically connected with the wiring layer; and one or more encapsulation layers encasing at least a portion of the supporting structure.

In some embodiments, the cable further comprises a proximal end and a distal end, and the thin-film neural interface is disposed at the distal end of the cable.

In some embodiments, the medical device further comprises: a connector disposed at the proximal end of the cable and electrically connected to the one or more conductive traces; and a neurostimulator or computing device electrically connected with the one or more electrodes via the connector, the one or more conductive traces, and the wiring layer.

In some embodiments, the second surface of the supporting structure is attached to the bottom portion of each strut of the plurality of struts via an adhesive.

In various embodiments, a neural interface deployment system is provided comprising: a delivery device; a stent disposed within the delivery device, the stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion, and wherein the top portion is in a retracted configuration within the delivery device at an angle that ranges from −30° to 10° relative to the base portion; and a cross-bar attached to the top portion of each strut of the plurality of struts; and a thin-film neural interface disposed within the delivery device, the thin-film neural interface comprising: a supporting structure; and one or more electrodes formed on the supporting structure, wherein the supporting structure is attached to the bottom portion of each strut of the plurality of struts.

In some embodiments, each strut of the plurality of struts have an elliptical or circular geometry.

In some embodiments, the base portion of each strut of the plurality of struts is an arc that is less than one half of a circumference of the elliptical or circular geometry, and wherein the top portion of each strut of the plurality of struts is an arc that is greater than one half of a circumference of the elliptical or circular geometry.

In some embodiments, the thin-film neural interface further comprises a wiring layer formed on the supporting structure, and the one or more electrodes are electrically connected to the wiring layer, and wherein the supporting structure comprises one or more layers of dielectric material.

In some embodiments, the neural interface deployment further comprises: a cable comprising: the supporting structure comprised of the dielectric material; one or more conductive traces formed on the supporting structure and electrically connected with the wiring layer; and one or more encapsulation layers encasing at least a portion of the supporting structure.

In various embodiments, a method of delivering a neural interface to a target biological structure is provided comprising: obtaining a neural interface deployment system: a delivery device; a stent disposed within the delivery device, the stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion, and wherein the top portion is in a retracted configuration within the delivery device at an angle that ranges from −30° to 10° relative to the base portion; and a cross-bar attached to the top portion of each strut of the plurality of struts; and a thin-film neural interface disposed within the delivery device, the thin-film neural interface comprising: a supporting structure; and one or more electrodes formed on the supporting structure, wherein the supporting structure is attached to the bottom portion of each strut of the plurality of struts; delivering, using the delivery device, the thin-film neural interface to the target biological structure; removing the delivery device from the stent and the thin-film neural interface; and deploying, using the stent, the thin-film neural interface, wherein the deploying comprises expanding the stent from the retracted configuration to an expanded configuration that places the one or more electrodes into contact with the target biological structure.

BRIEF DESCRIPTION OF THE DRAWINGS

The present disclosure will be better understood in view of the following non-limiting figures, in which.

DESCRIPTION

I. Introduction

Figure 1:
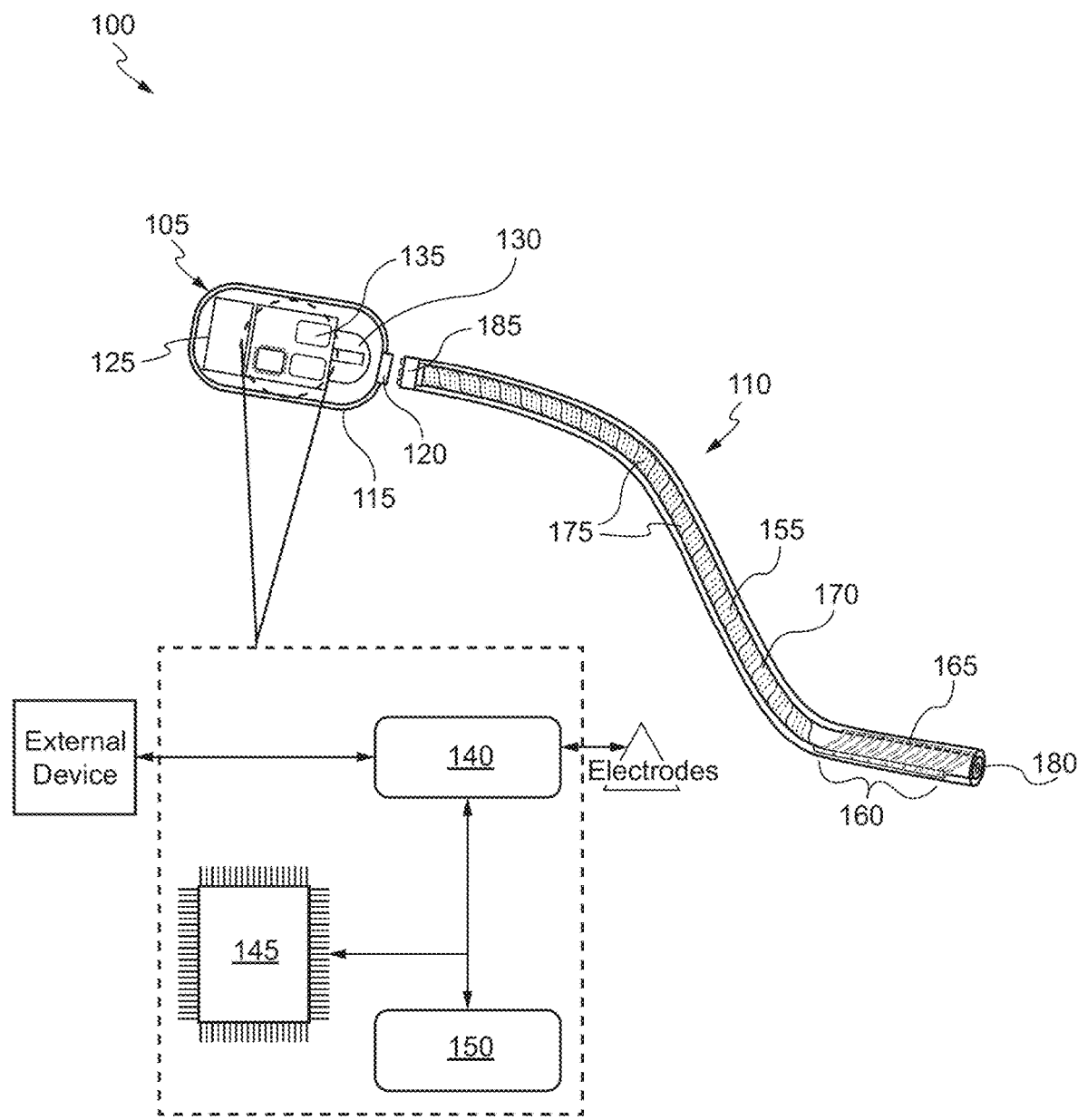
FIG. 1 shows a neuromodulation system according to various embodiments of the present disclosure.

The present disclosure describes a medical device comprising a self-expanding stent and a thin-film neural interface, methods of making a medical device comprising a self-expanding stent and a thin-film neural interface, and methods of delivering medical device comprising a self-expanding stent and a thin-film neural interface. In various embodiments, the medical device described herein comprises a self-expanding stent comprising a plurality of struts having a substantially elliptical or circular geometry arranged in series from a proximal end to a distal end of the stent, and a thin-film neural interface attached to the stent. Specifically, each strut of the self-expanding stent comprises a top portion and a base portion integrally connected with the top portion at a first connection point and a second connection point. Each of the struts form a first hinge at the first connection point and a second hinge at the second connection point, wherein the first hinge and the second hinge allow the top portion to move relative to the base portion. The self-expanding stent provides a retracted configuration to protect the thin-film neural interface during delivery to a target biological structure, and the self-expanding stent has an expanded configuration to deploy the thin-film neural interface at the target biological structure.

Conventionally, neuroprosthesis/BMI and neuromodulation technology in the brain is limited due the complexity and restricted channels to reach target biological structures in the brain. For example, a medical device that is delivered to the brain needs to be navigated through tight channels into the cerebral veins. Due to the constricted pathways to regions of the brain, electrodes and/or sensors on a neural interface are frequently damaged during delivery to a target biological structure. For example, a high-density electrode is frequently subjected to high stresses and/or strains when delivered to a target biological structure due to, for example, narrower vascular canals. The high stresses and/or strains on the electrode array can result in damage to the electrodes or the electrodes can be dislodged from the electrode array.

To address these limitations and problems associated with delivering a thin-film neural interface to the brain, the self-expanding stent comprising a thin-film neural interface of various embodiments disclosed herein comprises a plurality of struts having a specific structure that can collapse (e.g., retracted state) when loaded into the delivery system to protect the thin-film neural interface during delivery to a target location. For example, the self-expanding stent may comprise a plurality of angled struts that are equidistantly spaced to hinge from a retracted state to an expanded state. In the retracted state, the plurality of angled struts are stacked within a preceding loop to provide a substantially flat shape, thereby protecting the thin-film neural interface during delivery.

In some embodiments, the self-expanding stent can simultaneously satisfy a number of mechanical requirements. First, the stent is capable of withstanding the structural loads, namely radial compressive forces, imposed on the stent as it supports the walls of a vessel lumen. In addition to having adequate radial strength, the stent should be longitudinally flexible to allow it to be maneuvered through a tortuous vascular path and to enable it to conform to a deployment site that may not be linear or may be subject to flexure. The material from which the stent is constructed allows the stent to undergo expansion which typically requires substantial deformation of localized portions of the stent's structure. Once expanded, the stent maintains its size and shape throughout its service life despite the various forces. Finally, the stent is biocompatible so as not to trigger any adverse vascular responses.

In various embodiments, a medical device is provided that comprises: a stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion; a first cross-bar attached to the first connection point of each strut of the plurality of struts; a second cross-bar attached to the second connection point of each strut of the plurality of struts; and a third cross-bar attached to the top portion of each strut of the plurality of struts; and a thin-film neural interface comprising: a supporting structure having a first surface and a second surface opposite of the first surface; and one or more electrodes formed on the first surface of the supporting structure, wherein the second surface of the supporting structure is attached to the bottom portion of each strut of the plurality of struts.

In various embodiments, a neural interface deployment system is provided comprising: a delivery device; a stent disposed within the delivery device, the stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion, and wherein the top portion is in a retracted configuration within the delivery device at an angle that ranges from −30° to 10° relative to the base portion; and a cross-bar attached to the top portion of each strut of the plurality of struts; and a thin-film neural interface disposed within the delivery device, the thin-film neural interface comprising: a supporting structure; and one or more electrodes formed on the supporting structure, wherein the supporting structure is attached to the bottom portion of each strut of the plurality of struts.

In various embodiments, a method of delivering a neural interface to a target biological structure is provided comprising: obtaining a neural interface deployment system: a delivery device; a stent disposed within the delivery device, the stent comprising: a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move relative to the base portion, and wherein the top portion is in a retracted configuration within the delivery device at an angle that ranges from −30° to 10° relative to the base portion; and a cross-bar attached to the top portion of each strut of the plurality of struts; and a thin-film neural interface disposed within the delivery device, the thin-film neural interface comprising: a supporting structure; and one or more electrodes formed on the supporting structure, wherein the supporting structure is attached to the bottom portion of each strut of the plurality of struts; delivering, using the delivery device, the thin-film neural interface to the target biological structure; removing the delivery device from the stent and the thin-film neural interface; and deploying, using the stent, the thin-film neural interface, wherein the deploying comprises expanding the stent from the retracted configuration to an expanded configuration that places the one or more electrodes into contact with the target biological structure.

II. Neuroprosthesis/BMI Devices and Systems with a Thin-Film Neural Interface

FIG. 1 shows a neurostimulation/BMI system 100 in accordance with some aspects of the present disclosure. In various embodiments, the neurostimulation/BMI system 100 includes a computing device 105 and a thin-film lead assembly 110. In various embodiments, the computing device 105 can be implantable, semi-implantable, or an external system. The computing device 105 may include a housing 115, a feedthrough assembly 120, a power source 125, an antenna 130, and an electronics module 135. For applications where the computing device 105 is implanted, the housing 115 may be comprised of materials that are biocompatible such as bioceramics or bioglasses for radio frequency transparency, or metals such as titanium. In some embodiments, the size and shape of the housing 115 may be selected such that the computing device 105 can be implanted within a patient. In the example shown in FIG. 1, the feedthrough assembly 120 is attached to a hole in a surface of the housing 115 such that the housing 115 is hermetically sealed. The feedthrough assembly 120 may include one or more feedthroughs (i.e., electrically conductive elements, pins, wires, tabs, pads, etc.) mounted within and extending through the surface of the housing 115 or a cap from an interior to an exterior of the housing 115. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to conductive traces of the thin-film lead assembly 110 connected to exterior ends of the feedthrough assembly 120. The electronics module 135 may include discrete and/or integrated electronic circuit components that implement analog and/or digital circuits capable of producing the functions attributed to the neuromodulation or BMI devices or systems such as applying neural stimulation to a patient or sensing and recording electrical activity from a patient. In various embodiments, the electronics module 135 may include software and/or electronic circuit components such as a pulse generator 140 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), causes delivery of the stimulation via the pulse generator 140 and electrodes, and/or records the determined or sensed electrical activity in a storage device, and a memory 150 with program instructions operable on by the pulse generator 140 and the controller 145 to perform one or more processes for: (i) applying or delivering neural stimulation, or (ii) translating neuronal information into commands capable of controlling external software or hardware such as a computer or robotic arm.

In various embodiments, the thin-film lead assembly 110 is a monolithic structure that includes a cable 155 or lead body and a thin-film neural interface 160. In some embodiments, the thin-film neural interface 160 is attached to a portion of a stent 165. For example, the thin-film neural interface 160 may be removably attached to a base portion of the stent 165. In some embodiments, the thin-film neural interface 160 comprises a thin-film structure having one or more electrodes 162 (i.e., recording electrodes, neurostimulation electrodes, sensors, or combinations thereof). In some embodiments, the thin-film neural interface 160 is formed at a distal end of the cable 155. The thin-film neural interface 160 may be formed from the same supporting structure 170 as the cable 155. The supporting structure 170 includes a base dielectric material such as a polymer having suitable dielectric, flexibility and biocompatibility characteristics that provides support for microelectronic structures including conductive traces 175, electrodes 162, wiring layers 180, optional contacts, etc. The wiring layer 180 may be used to directly or indirectly electrically connect the electrodes 162 with the one or more conductive traces 175. The conductive traces 175 may be used to directly or indirectly electrically connect the electrodes 162 with the electronics module 135. The term "directly", as used herein, may be defined as being without something in between. The term "indirectly", as used herein, may be defined as having something in between.

In some embodiments, the thin-film lead assembly 110 further includes a connector 185. In certain embodiments, the connector 185 is bonding material that bonds conductor material of the cable 155 to the electronics module 135 of the computing device 105 via the feedthrough assembly 120. The bonding material may be a conductive epoxy or a metallic solder or weld such as platinum. In other embodiments, the connector 185 is conductive wire, conductive traces, or bond pads (e.g., a wire, trace, or bond pads formed of a conductive material such as copper, silver, or gold) formed on a substrate and bonds a conductor of the cable 155 to the electronics module 135 of the computing device 105. In alternative embodiments, the computing device 105 and the cable 155 are designed to connect with one another via a mechanical connector 185 such as a pin and sleeve connector, snap and lock connector, flexible printed circuit.

III. Self-Expanding Stent

Figure 2:
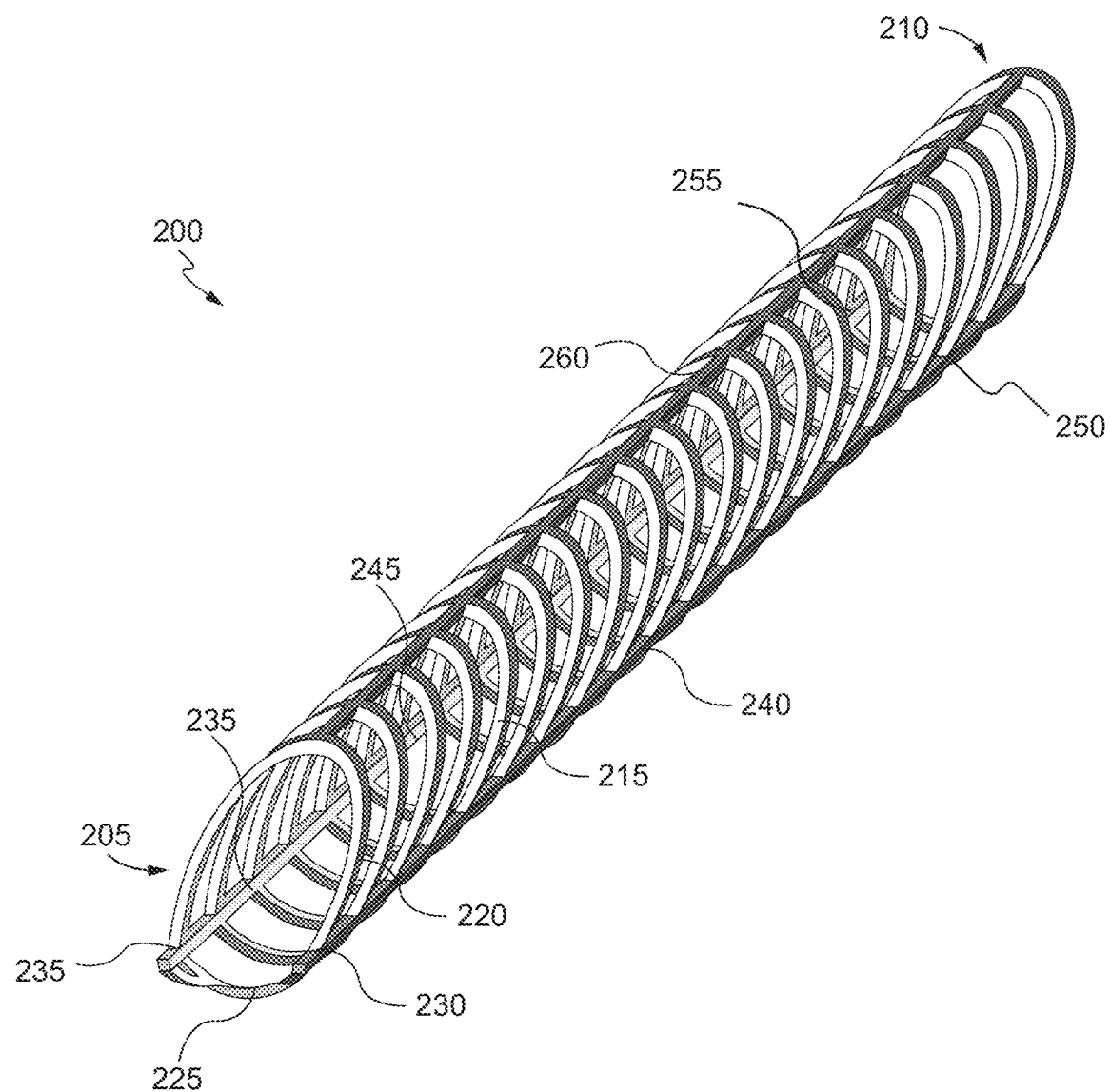
FIG. 2 shows a perspective view of a self-expanding stent according to various embodiments of the present disclosure.

FIG. 2 shows a perspective view of a self-expanding stent 200 according to various embodiments of the present disclosure. In some embodiments, a self-expanding stent 200 is provided for delivering a thin-film neural interface to a target biological structure. The thin-film neural interface (not shown) can be removably attached to the self-expanding stent 200. The self-expanding stent 200 relates to a radially expandable endoprostheses, which is adapted to be implanted in a bodily lumen. An "endoprosthesis" corresponds to an artificial device that is placed inside the body. A "lumen" refers to a cavity of a tubular organ such as a blood vessel. In some instances, the self-expanding stent 200 is generally cylindrically shaped device, which functions to hold open and sometimes expands a segment of a blood vessel or other anatomical lumen.

The self-expanding stent 200 includes a scaffolding that includes a pattern or network of interconnecting structural elements. As shown in FIG. 2, the self-expanding stent 200 comprises a plurality of struts 215 arranged in series from a proximal end 205 to a distal end 210 of the stent 200. As used herein, the term "proximal end" refers to a first end of the stent, while the term "distal end" refers to a second end opposing the first end. For example, the proximal end 205 may be an end of the stent, which is closest to the user, and the distal end 210 may be an end of the stent, which is furthest from the user. Each of the struts 215 comprises a top portion 220 and a base portion 225. In some embodiments, the top portion 220 of the stent is integrally connected to the base portion 225. For example, the top portion 220 and the base portion 225 may be laser-cut from a single flexible material. In some embodiments, the self-expanding stent 200 is formed from a shape-memory material. The shape-memory material may comprise stainless steel, Nitinol, nickel, titanium, or any combinations thereof. As used herein, "shape memory material" refers to materials that retain their original shape when exposed to certain conditions (e.g., temperature or pressure). In some instances, the self-expanding stent 200 is designed to collapse or expand under certain conditions (e.g., under an applied radial force). In some instances, the self-expanding stent 200 is laser cut from a shape-memory material. For example, the self-expanding stent 200 is laser cut from a Nitinol tube.

In some embodiments, each strut 215 of self-expanding stent 200 has a substantially elliptical or circular geometry. As used herein, the terms "substantially," "approximately," and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. For example, each strut 215 (comprising the top portion 220 and base portion 225) can be oval-shaped. In some embodiments, the top portion 220 of each strut 215 has an arc greater than one half of the circumference of the elliptical or circular geometry of the strut 215. For example, the top portion 220 of each strut 215 is greater than 50% of a circumference of the elliptical or circular geometry of the strut 215, e.g., greater than 55%, greater than 60%, greater than 65%, greater than 70%, greater than 75%, greater than 80%, greater than 85%, or greater than 90%. In some embodiments, the base portion 225 of each strut 215 of has an arc that is less than one half of the circumference of the elliptical or circular geometry of the strut 215. For example, the base portion 225 of each strut 215 has an arc that is less than 50% of the circumference of the elliptical or circular geometry of the strut 215, e.g., e.g., less than 45%, less than 40%, less than 35%, less than 30%, less than 25%, less than 20%, less than 15%, or less than 10%.

In some embodiments, the self-expanding stent 200 comprises a plurality of struts 215 arranged in series. For example, each strut may arranged successively one after another in sequential order. In some embodiments, the self-expanding stent comprises 2 or more struts, e.g., 3 or more struts, 4 or more struts, 5 or more struts, 6 or more struts, 7 or more struts, 8 or more struts, 9 or more struts, or 10 or more struts. In some embodiments, each strut 215 is spaced at a predetermined distance from an adjacent strut. In some embodiments, the predetermined distance is at least 0.5 mm, e.g., at least 0.6 mm, at least 0.7 mm, at least 0.8 mm, at least 0.9 mm, or at least 1.0 mm. In some embodiments, the each strut 215 is spaced at varying distances from an adjacent strut. For example, an initial strut (e.g., first strut at the proximal end 205 of the stent) and a terminal strut (e.g., last strut at the distal end 210 of the stent) may be spaced at first distance from an adjacent strut, and the remaining struts between the initial strut and the terminal strut may be spaced at a second distance that is different from the first distance.

As shown in FIG. 2, the top portion 220 of the self-expanding stent 200 can be integrally connected to the base portion 225. In some embodiments, the top portion 220 can be integrally connected to the base portion 225 at a first connection point 230 and a second connection point 235. In some embodiments, the first connection point 230 and the second connection point 235 are regions of the stent where the top portion 220 and the base portion 225 intersect or meet, thereby providing a monolithic structure. The self-expanding stent 200 may comprise a first cross-bar 240 and a second cross-bar 245 that is integrally formed between the top portion 220 and the base portion 225. The first cross-bar 240 and the second cross-bar 245 may be formed on opposing sides of the self-expanding stent 200. For example, each strut 215 of self-expanding stent 200 has a substantially elliptical or circular geometry in which portion of the circumference of the elliptical or circular geometry of the strut 215 is the top portion 220 and the base portion 225. In this respect, the first cross-bar 240 and the second cross-bar 245 delineates the top portion 220 from the base portion 225. In some embodiments, the top portion 220 is disposed at an acute angle with respect to the first cross-bar 240 and the second cross-bar 245. In some embodiments, the base portion 220 is disposed substantially at a 900 angle with respect to the first cross-bar 240 and the second cross-bar 245.

In some embodiments, the first cross-bar 240 may be substantially parallel to the second cross-bar 245. For example, the top portion 220 and the second cross-bar 245 can be formed on opposing sides of the self-expanding stent 200 and are parallel to one another. In some embodiments, the first cross-bar 240 and the second cross-bar 245 extend through the first connection point 230 and the second connection point 235 of each strut 215 to form a first hinge 250 and a second hinge 255. The first hinge 250 and the second hinge 255 allow the top portion 220 to move relative to the base portion 225. In some embodiments, the first hinge 250 and the second hinge 255 allow the top portion 220 to move at an angle relative to the base portion 225 ranging from −30° to 90°, e.g., −25° to 85°, −20° to 80°, −15° to 75°, −10° to 70°, −5° to 65°, 0° to 65°, 0° to 60°, 5° to 55°, or −10° to 50°. In some instances, the first cross-bar 240 and the second cross-bar 245 includes a projection formed at the distal end 210 of the self-expanding stent 200. The projection may include an enclosed aperture that accommodates tools for grasping the self-expanding stent 200.

In some embodiments, the self-expanding stent 200 includes a third cross-bar 260 attached to the top portion 220 of each strut 215. The third cross-bar 260 extends from the proximal end 205 to the distal end 210 of the self-expanding stent 200. For example, third cross-bar 260 extends from the apex of the initial strut to the apex of the terminal strut. The third cross-bar 260 provides rigidity to the self-expanding stent 200 to allow the top portion 220 to move uniformly with respect to the base portion 225. For example, when the self-expanding stent 200 is compressed in a delivery sheath, the top portion 220 will move at the first hinge 250 and the second hinge 255 to flatten the top portion 220 of the stent 200. The third cross-bar 260 allows the top portion 220 to move uniformly towards the base portion 225. In some embodiments, the self-expanding stent 200 may comprise a plurality of cross-bars (other than the first cross-bar 240 and second cross-bar 245) to provide rigidity to the top portion 220 of the self-expanding stent 200. For example, the self-expanding stent 200 may comprise two or more cross-bars, e.g., three or more cross-bars, four or more cross-bars, five or more cross-bars, six or more cross-bars, or seven or more cross-bars.

Figure 3A:
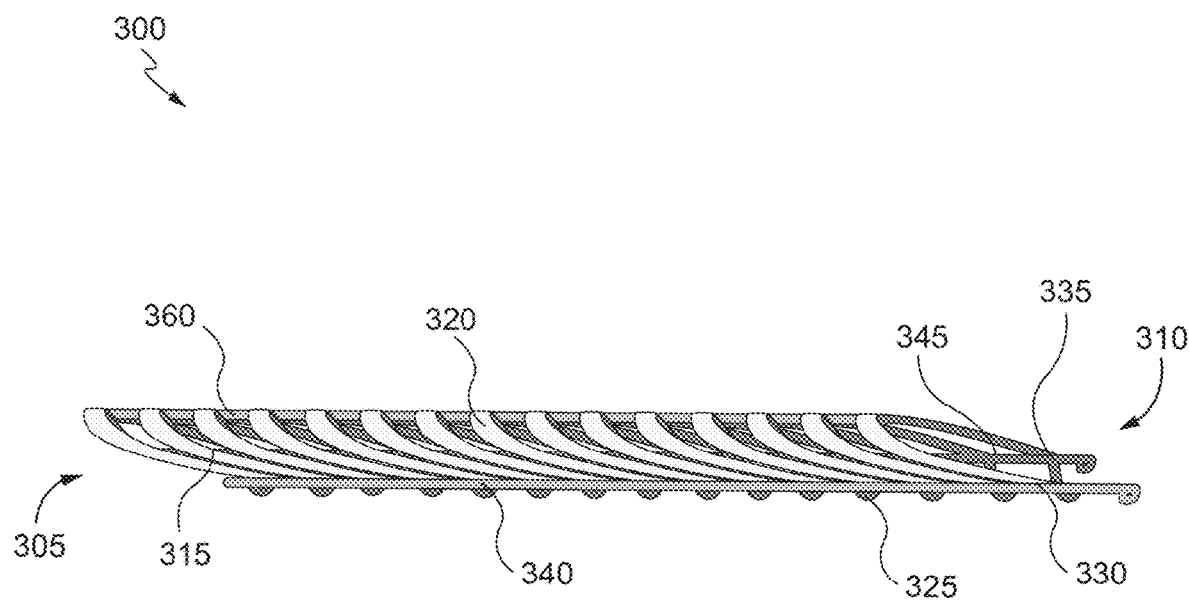
FIGS. 3A and 3B show multiple views of a self-expanding stent in a retracted state according to various embodiments of the present disclosure.
Figure 3B:
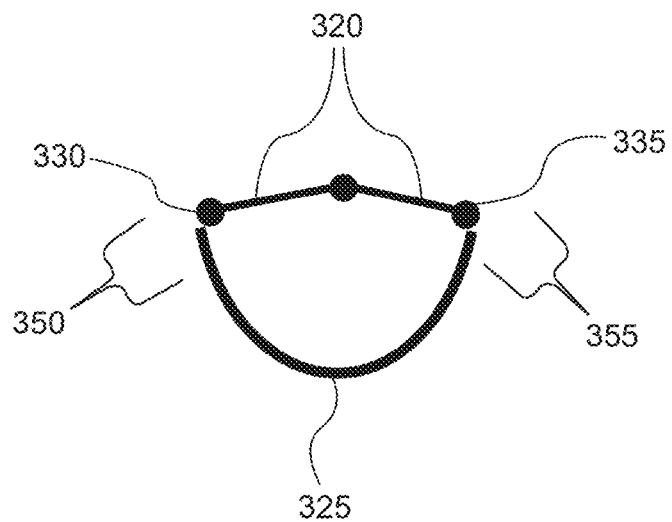

FIGS. 3A and 3B show multiple views of the self-expanding stent 300 (e.g., the self-expanding stent 200 described with respect to FIG. 2) in a retracted state according to various embodiments of the present disclosure. The self-expanding stent 300 comprises a proximal end 305 and a distal end 310. Each of the struts 315 are disposed between the proximal end 305 and the distal end 310. In some embodiments, the self-expanding stent 300 is comprised of a plurality of interconnecting struts 315 that forms a generally tubular-shaped interior volume. In some embodiments, the struts 315 function to hold open a segment of a blood vessel or other body lumen such as a super cerebral vein. In some embodiments, the stent 300 is initially maintained in a radially compressed or collapsed state as shown in FIG. 3A to enable it to be maneuvered through the lumen. Once in position, the self-expanding stent 300 can be deployed from a delivery device and expands to its original configuration.

When deployed, the stent 300 is maintained in a radially expanded state to enable it to deliver a thin-film neural interface to a target biological structure.

FIG. 3A shows the self-expanding stent 300 in a retracted state in accordance with various embodiments. In some embodiments, the top portion 320 of the stent 300 moves with respect to the base portion 325 when an external force is applied to the stent 300. For example, when the self-expanding stent 300 is inserted into a delivery device (e.g., a delivery sheath, a catheter, etc.), the external force from the delivery device forces the top portion 320 of the stent 300 to move towards the base portion 325. In some embodiments, the top portion 320 of each of the struts 315 moves at a first connection point 330 and a second connection point 335 between the top portion 320 and the base portion 325. The first cross-bar 340 and the second cross-bar 345 extend through the first connection point 330 and the second connection point 335 of each strut 315 to form a first hinge 350 and a second hinge 355 (shown in FIG. 3B). The first hinge 350 and the second hinge 355 allow the top portion 320 to move relative to the base portion 325.

FIG. 3B shows a cross-sectional view of the self-expanding stent 300 in a retracted state in accordance with various embodiments. In the retracted state, the first hinge 350 and the second hinge 355 allow the top portion 320 to move at an angle relative to the base portion 325. At the first hinge 350 and the second hinge 355, the top portion 320 of the stent 300 moves towards the base portion 325 when an external load is applied. In some embodiments, the angle of the top portion 320 relative to the base portion 325 ranges from −30° to 20° in the retracted state, e.g., −25° to 15°, −20° to 10°, −30° to 10°, −25° to 5°, −20° to 10°, −10° to 10°, −10° to 5°, −10° to 0°, or −5° to 5°.

In some embodiments, the top portion 320 is substantially parallel with the first cross-bar 340 and the second cross-bar 345 in the retracted state. In some embodiments, the angle of the top portion 320 relative to the first cross-bar 340 and the second cross-bar 345 ranges from −30° to 20° in the retracted state, e.g., −25° to 15°, −20° to 10°, −30° to 10°, −25° to 5°, −20° to 10°, −10° to 10°, −10° to 5°, −10° to 0°, or −5° to 5°. In some embodiments, the height of the entire stent 300 in the retracted state is reduced by at least one half due to the movement of the top portion 320 towards the base portion 325. For example, the height of the entire stent 300 is reduced by greater than 50% in the retracted state, e.g., greater than 55%, greater than 60%, greater than 65%, greater than 75%, or greater than 80%. In certain aspects, the base portion 325 of the struts 315 is not subject to substantial flexure as the top portion 320 of the stent 300 is moving with respect to the base portion 325. For example, the base portion 325 may only be subject to minimal compressive forces of a delivery device. Therefore, a thin-film neural interface attached to the base portion 325 of the stent 300 has limited deformation during delivery.

Figure 4A:
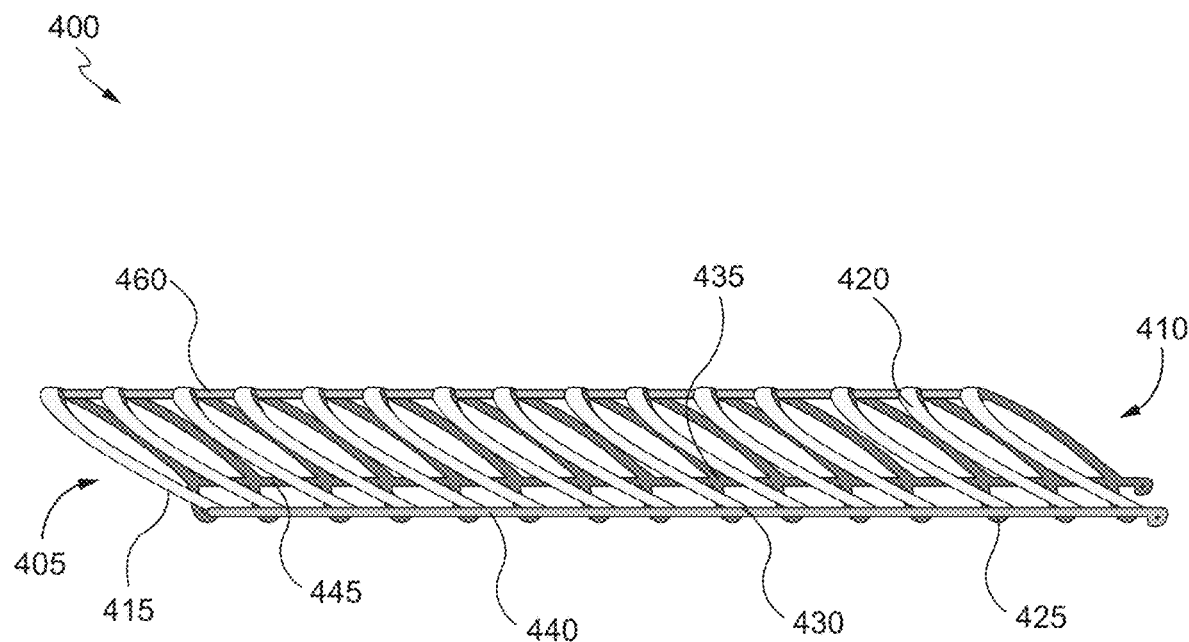
FIGS. 4A and 4B show multiple views of a self-expanding stent in an expanded state according to various embodiments of the present disclosure.
Figure 4B:
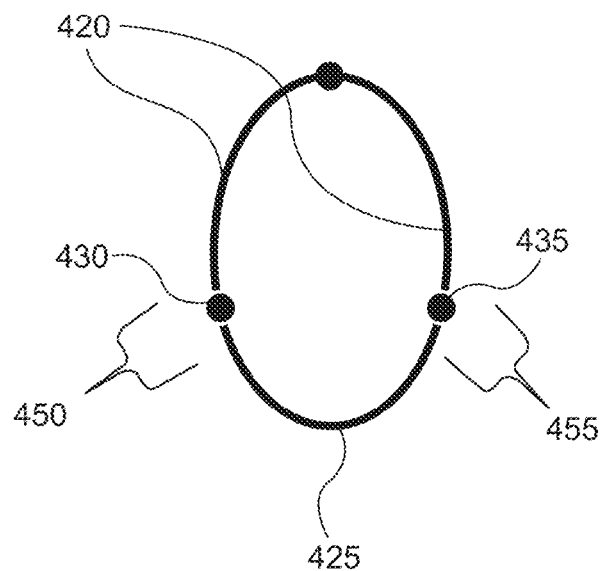

FIGS. 4A and 4B show multiple views of the self-expanding stent 400 (e.g., the self-expanding stent 200 described with respect to FIG. 2) in an expanded state according to various embodiments of the present disclosure. In some embodiments, the top portion 420 of the struts 415 of the stent 400 may collapse during insertion of the stent 400 in a subject (e.g., a human patient), and the stent 400 may be expand to take the shape of a surrounding body lumen when deployed in the subject. In certain instances, the stent 400 may be adapted to expand when deployed out of an end of a delivery device such as a delivery sheath disposed around the stent 400. In certain instances, the stent 400 may expand from a retracted state to an expanded state that places a thin-film neural interface into contact with the target biological structure. The struts 415 of the stent 400 function to hold open a segment of a blood vessel or other body lumen such as a super cerebral vein.

FIG. 4A shows the self-expanding stent 400 in an expanded state in accordance with various embodiments. In the expanded state, the first hinge 450 and the second hinge 455 biases the top portion 420 away from the base portion 425. For example, the stent 400 may be cut from a shape-memory material (e.g., Nitinol tube) to have a geometry described herein with a first hinge 450 and a second hinge 455 that biases the top portion 420 of the struts 415 away from the base portion 425. In the expanded state, the stent 400 may have a maximum height. In some embodiments, the top portion 420 forms an acute angle with respect to the first cross-bar 440 and the second cross-bar 445 in the expanded state. In some embodiments, the angle of the top portion 420 relative to the base portion 425 ranges from 20° to 90° in the expanded state, e.g., 25° to 85°, 30° to 85°, 35° to 75°, 40° to 80°, 45° to 75°, 50° to 70°, 30° to 80°, 40° to 80°, or 50° to 85°. In some embodiments, the angle of the top portion 420 relative to the first cross-bar 440 and the second cross-bar 445 ranges from 20° to 90° in the expanded state, e.g., 25° to 85°, 30° to 85°, 35° to 75°, 40° to 80°, 45° to 75°, 50° to 70°, 30° to 80°, 40° to 80°, or 50° to 85°.

FIG. 4B shows a cross-sectional view of the self-expanding stent 400 in an expanded state in accordance with various embodiments. In some embodiments, the interior volume of the stent 400 is substantially tubular. In some embodiments, the self-expanding stent 400 comprises a generally elliptical or circular cross-section formed by the plurality of interconnecting struts 415. In some embodiments, the stent 400 has a larger cross-sectional area for each strut 415 (e.g., the top portion 420 and base portion 425 of the struts 415 taken together) in the expanded state relative to the retracted state. In some embodiments, the cross-sectional area for each strut 415 in the expanded state is at least 50% greater than the cross-sectional area for each strut 415 in the retracted state, e.g., greater than 55%, greater than 60%, greater than 65%, greater than 70%, greater than 75%, greater than 80%, greater than 85%, or greater than 90%. In the expanded state, the stent 400 maintains a radially expanded state to hold open a segment of a blood vessel or other body lumen to enable it to deliver a thin-film neural interface to a target biological structure.

IV. Medical Device

Figure 5A:
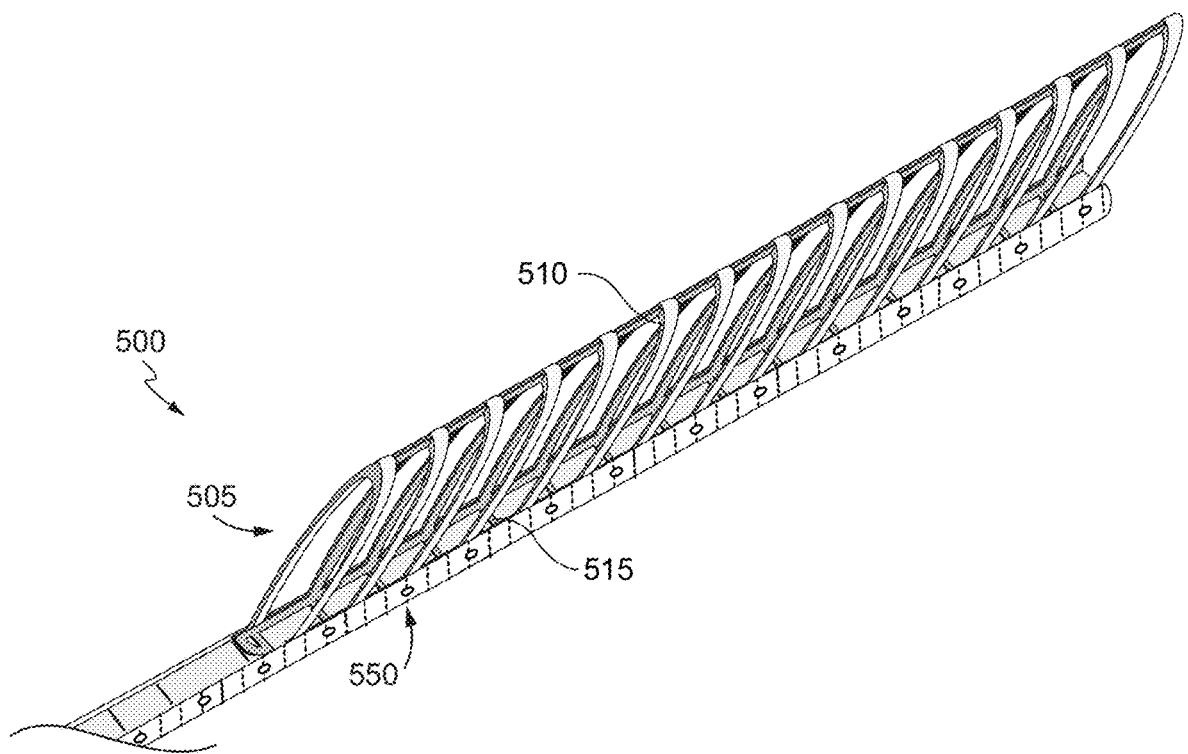
FIGS. 5A and 5B shows a medical device array including a thin-film neural interface and a cross-sectional view of the thin-film neural interface, respectively, according to various embodiments of the present disclosure.
Figure 5B:
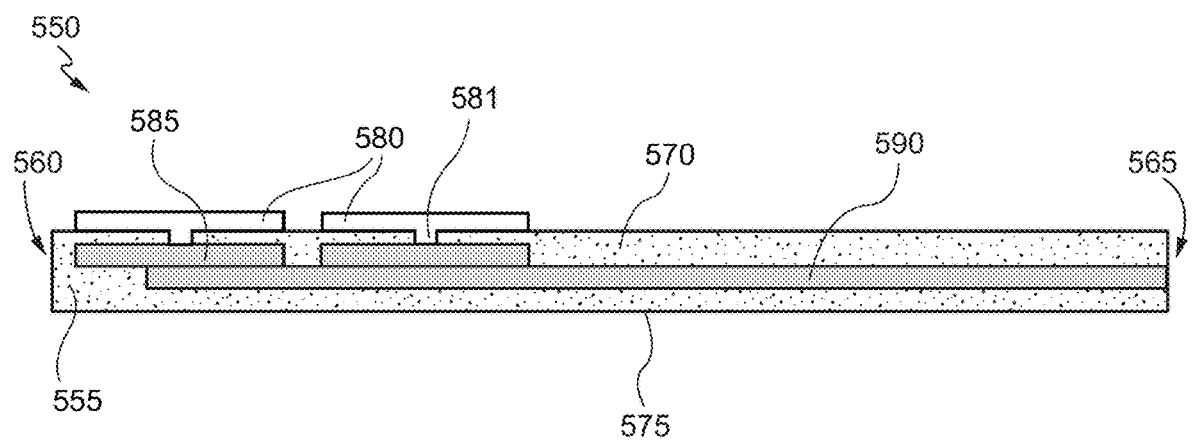

FIGS. 5A and 5B show a medical device 500 according to various embodiments of the present disclosure. As shown in FIG. 5A, the medical device 500 comprises a self-expanding stent 505 (as described in FIGS. 1, 2, 3A, 3B, 4A, and 4B) and a thin-film neural interface 550. In some embodiments, the thin-film neural interface 550 may be removably attached to the self-expanding stent 505. For example, the thin-film neural interface 550 is attached to the bottom portion of one more the struts 510 of the self-expanding stent 505 using an adhesive (e.g., curable adhesive), welding, or a conductive epoxy. In some embodiments, the thin-film neural interface 550 may be integrally formed with the self-expanding stent 505. For example, one or more layers of the thin-film neural interface 550 may be melted and reflowed (thermal reflow) to completely encase or partially encase a portion of the self-expanding stent 505. In certain instances, the thin-film neural interface 550 is integrally attached a bottom portion of one more the struts 510 of the self-expanding stent 505. In certain aspects, the thin-film neural interface 550 is attached to the base portion 515 of the self-expanding stent 505.

As shown in FIG. 5B, the thin-film neural interface 550 comprises a supporting structure 555. The supporting structure 555 extends from the proximal end 560 to the distal end 565 of the thin-film neural interface. The supporting structure 555 is made of one or more layers of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. For example, the dielectric material may be a polymer of imide monomers (i.e., a polyimide), a liquid crystal polymer (LCP) such as Kevlar®, parylene, polyether ether ketone (PEEK), or combinations thereof. In certain instances, the supporting structure 555 comprises one or more layers of LCP.

The supporting structure 555 comprises a first surface 570 and a second surface 575 opposite the first surface. The first surface 570 may support microelectronics (e.g., electrodes) and the second surface 575 of the supporting structure 555 may be attached to the self-expanding stent 550. The second surface 575 of the supporting structure 555 can be attached to the self-expanding stent 505 in various ways. In some embodiments, the second surface 575 of the supporting structure 555 may be removably attached to the self-expanding stent 505. For example, the second surface of the supporting structure 555 is attached to the bottom portion of one more the struts 510 (e.g., the base portion 515 of one or more struts 510) of the self-expanding stent 505 using an adhesive (e.g., curable adhesive), welding, or a conductive epoxy. In some embodiments, the second surface 575 of the supporting structure 555 may be integrally formed with the self-expanding stent 505. The one or more layers of the supporting structure 555 adjacent the second surface 575 can melted and reflowed (thermal reflow) to encase completely or partially the stent in the one or more layers of the supporting structure 555. For example, one or more layers of dielectric mater may be heated to a given melting temperature (the thin-film structure does not liquefy because it comprises a polymer (e.g., LCP) with a higher reflow temperature than the given temperature) and completely encases a bottom portion of the struts 510 of the self-expanding stent 505. Thereafter, the medical device 500 is cooled (e.g., at ambient temperature) to obtain the integrally bonded thin-film interface and stent.

One more or more electrodes 580 can be formed on the first surface 570 of the supporting structure 555. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 555 provides support for microelectronic structures including one or more electrodes 580, a wiring layer 585, and one or more conductive traces 590. Optionally, the supporting structure 555 may include contacts 581 formed on and within the supporting structure to the portion of the top surface the wiring layer 585. The wiring layer 585 electrically connects each of the one or more electrodes 580 to the one or more conductive traces 590. In some embodiments, the pattern of electrodes 580 may include each electrode 580 spaced apart from one another via a portion or region of the dielectric layers. It should be understood by those of skill in the art that different patterns are also contemplated by the present disclosure.

In some embodiments, the electrodes 580 can be comprised of a metal, an alloy, platinum and/or platinum iridium. In some embodiments, the electrodes 580 can have a rectangular shape, though it will be appreciated that other shapes (e.g., circular, square, oval, etc.) are contemplated as well. In certain embodiments, the electrodes 580 have a width that is at least 0.05 mm, at least 0.1 mm, or at least 0.5 mm. In certain embodiments, the electrodes 580 have a width that is less than 1 mm, less than 2 mm, or less than 5 mm. In certain embodiments, the electrodes 580 have a length that is at least 0.5 mm, at least 1 mm or at least 2 mm. In certain embodiments, the electrodes 580 have a length that is less than 20 mm or less than 10 mm. In certain embodiments, the electrodes 580 may be arranged to form multiple rows of electrodes 580, where each row includes a subset of the set of electrodes. In the depicted instance, each row includes four electrodes, though it will be appreciated that other quantities are contemplated. For example, each row may include at least 2, at least 3, or at least 5 electrodes and/or less than 5, less than 10, or less than 15 electrodes.

In various embodiments, the one or more conductive traces 590 are a plurality of traces, for example, two or more conductive traces or from two to forty-eight conductive traces (e.g., one conductive trace for each electrode/sensor). The plurality of conductive traces 590 are comprised of one or more layers of conductive material. The conductive material selected for the one or more conductive traces 590 should have good electrical conductivity and may include pure metals, metal alloys, combinations of metals and dielectrics, and the like. For example, the conductive material may be copper (Cu), gold (Au), silver (Ag), gold/chromium (Au/Cr), etc. In some embodiments, it is also desirable that the conductive material selected for the one or more conductive traces 590 have thermal expansion characteristics or a coefficient of thermal expansion (CTE) that is approximately equal to that of CTE of the supporting structure 555. Matching the CTE of components that contact one another is desirable because it eliminates the development of thermal stresses, which may occur during fabrication and the operation of the cable, and thus eliminates a known cause of mechanical failure in the components.

The one or more conductive traces 590 may be deposited onto a surface of the supporting structure 555 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 590 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structure 555. If, however, a signal plane having a relatively low impedance is desired, a greater thickness of electrically conductive material should be deposited onto the supporting structure 555. In certain embodiments, each of the one or more conductive traces 590 has a thickness (d). In some embodiments, the thickness (d) is from 0.5 μm to 100 μm or from 25 μm to 50 μm, for example about 25 μm or about 40 μm. In some embodiments, each of the one or more conductive traces 590 has a length (m) of about 5 cm to 200 cm or 50 cm to 150 cm, e.g., about 80 cm. In certain embodiments, each of the one or more conductive traces 590 extends from the proximal end 560 to the distal end 565. In some embodiments, each of the one or more conductive traces 560 has a width (y) from 2.0 μm to 500 μm, for example about 30 μm or about 50 μm.

In some embodiments, the thin-film neural interface 550 may be configured to curl along a first dimension 595, such that the thin-film neural interface 550 can at least partly wrap around the self-expanding stent 505. For example, the thin-film neural interface 550 can have a curvature that facilities attachment to the elliptical or circular geometry of the self-expanding stent 505. In certain aspects, the curvature of the thin-film neural interface 550 substantially corresponds to the arc of the base portion 515 of the self-expanding stent 505. In some instances, the thin-film neural interface 550 includes a curved shape and/or curved default shape. The thin-film neural interface 550 may be flexible to allow at least intermittent partial straightening during delivery of the thin-film neural interface 550.

Figure 6:
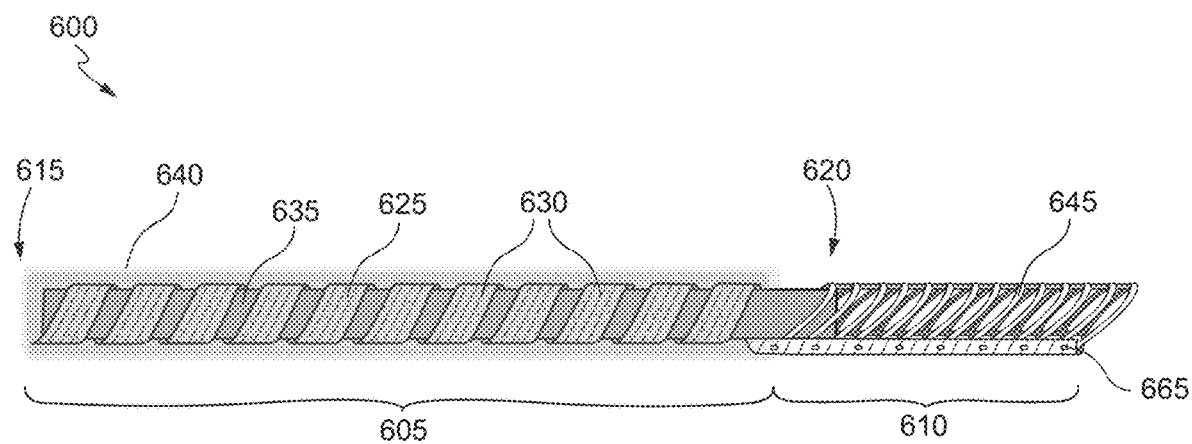
FIG. 6 shows a medical device according to another embodiment of the present disclosure.

FIG. 6 shows a medical device comprising a cable according to various embodiments of the present disclosure. In some embodiments, the medical device 600 comprises a cable 605. The thin-film neural interface 610 can be electrically connected to the cable 605. The cable 605 may comprise a proximal end 615 and a distal end 620. In some embodiments, the thin-film neural interface 610 is disposed at the distal end 620 of the cable 605.

The cable 605 may comprise a supporting structure 625 and one or more conductive traces 630 formed on a portion of the supporting structure 625. In some embodiments, the supporting structure 625 extends from the proximal end 615 to the distal end 620. In various embodiments, the supporting structure 625' of the thin-film neural interface 610 and the supporting structure 625 of the cable are the same structure (i.e., the supporting structure is continuous), which creates a monolithic structure. In some instances, the wiring layer 655 may be formed continuously with the one or more conductive traces 630. For example, each of the one or more conductive traces 630 may extend from the supporting structure 625 of the cable 605 through the supporting structure 625' of the thin-film neural interface 610 (as the wiring layer 655) and terminate at one or more of the electrodes 650.

In various embodiments, the supporting structure 625/625' has a thickness (t). In some embodiments, the thickness (t) is from 10 μm to 950 μm, for example about 150 μm or about 500 μm. In some embodiments, the supporting structure 625/625' has a length (l) of 5 cm to 150 cm or 50 cm to 100 cm, e.g., about 75 cm. In some embodiments, the supporting structure 625/625' has a width (w) from a first side to a second side. In some embodiments, the width (w) is from 0.5 mm to 5 mm, for example about 0.6 mm or about 5 mm.

In some embodiments, the cable 605 may further comprise a base tube 635. The base tube 635 may be comprised of a medical grade polymer material. In certain instances, the medical grade polymer is a soft polymer such as silicone. The supporting structure 625 and conductive traces 630 may be helically wrapped around the base tube 635. As used herein, the phrases "helical" or "helically wrapped" refer to a device fabricated with plural helixes or helices, which are a type of smooth space curve, i.e. a curve in three-dimensional space. The helixes may be wrapped in a clockwise direction or anti-clockwise direction. The helixes have the property that a tangent line at any point makes a constant angle with a fixed line called the axis.

The cable 605 may further comprise one or more encapsulation layers 640. The one or more encapsulation layers 640 may completely encase at least a portion of the supporting structure 625 and the one or more conductive traces 630. The one or more encapsulation layers 640 may be comprised of a medical grade polymer material. In some embodiments, the medical grade polymer is thermosetting plastic or thermoplastic. For example, the medical grade polymer may be a soft polymer such as silicone, a polymer dispersion such as latex, a chemical vapor deposited poly (p-xylylene) polymer such as parylene, or a polyurethane such as Bionate® Thermoplastic Polycarbonate-urethane (PCU) or CarboSil® Thermoplastic Silicone-Poly carbonate-urethane (TSPCU).

In various embodiments, the thin-film neural interface 610 comprises one or more encapsulation layers. In some embodiments, the one or more encapsulation layers 640 of the cable 605 and the one or more encapsulation layers of the thin-film neural interface 610 are the same structure (i.e., the encapsulation layer is continuous through the medical device 600), which creates a monolithic medical device 600. However, the one or more encapsulation layers of the thin-film neural interface 610 are not disposed over at least a portion of the self-expanding stent 645 such that the one or more electrodes 650 can directly interface with a biological structure. Additionally, the one or more encapsulation layers of the thin-film neural interface 610 are not disposed over at least a portion of the self-expanding stent 645 such that the top portion of the self-expanding stent 645 can expand. Consequently, the one or more encapsulation layers 640 of the thin-film neural interface 610 may have less layers of material (e.g., polymer) as compared to the one or more encapsulation layers 640 of the cable 605.

V. Method of Delivery

Figure 7:
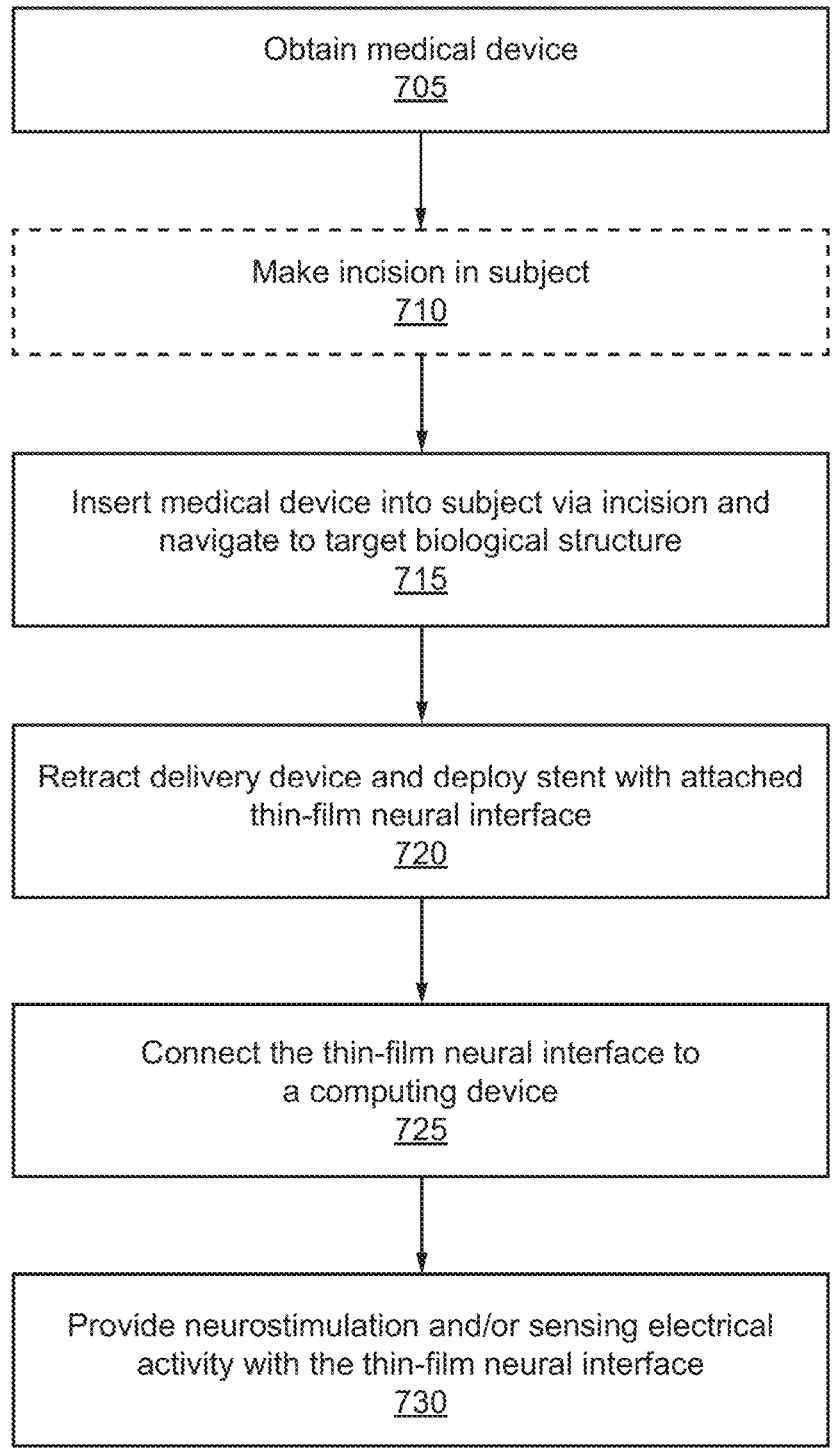
FIG. 7 shows a simplified flowchart depicting processing performed for accessing a site of a target biological structure and delivering a medical device or system for neurostimulation or interfacing to the site of the target biological structure in accordance with various embodiments.

FIG. 7 depicts a simplified flowchart depicting processing performed for accessing a site of a target biological structure in a patient and delivering a medical device or system for neurostimulation or interfacing to the site of the target biological structure according to various embodiments. As noted herein, the flowchart of FIG. 7 illustrates the architecture, functionality, and operation of possible implementations of systems, devices, and methods described with respect to FIGS. 1, 2, 3A, 3B, 4A, 4B, 5A, 5B, and 6. In this regard, each block in the flowchart or block diagrams comprises one or more processes or procedures. It should also be noted that, in some alternative implementations, the processes or procedures noted in each block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented manually by a user such as a surgeon or by special purpose hardware-based systems that perform the specified functions or acts, or combinations of special purpose hardware and computer instructions stored on a non-transitory storage medium.

In various embodiments, a delivery system includes a self-expanding stent, a thin-film neural interface attached (e.g., removably attached to the stent), and a delivery device (e.g., a delivery sheath). The thin-film neural interface can be removably attached to the stent using a standard medical grade adhesive. In an expanded state, the self-expanding stent allows the thin-film neural interface to be implanted within a bodily lumen (e.g., blood vessels). For example, the self-expanding stent expands such that the thin-film neural interface is pressed in intimate contact with a blood vessel wall. In some embodiments, the self-expanding stent is laser cut from a nitinol tube that is designed with a plurality of struts arranged in series that can collapse to fit into a delivery system (e.g., a delivery sheath) to provide a retracted state and an expanded state. For example, due to radial force, a portion of the stent collapses while loaded into a delivery system, which protects the thin-film neural interface, which cannot withstand the same strains as the stent itself. In some embodiments, in an expanded state, the stent applies minimal pressure to the blood vessel wall, which minimizes the risk of trauma or stenosis. In certain instances, the delivery system allows for transvascular placement within the brain of a thin-film neural interface including a high-density electrodes (e.g., for recording signals from one or more nerves or neurons and/or for delivering stimuli to one or more nerves or neurons).

FIG. 7 shows a method of delivering a thin-film lead assembly to a target biological structure using a delivery system. At step 705, a self-expanding stent including one or more thin-film neural interfaces is placed within a delivery device (e.g., a delivery sheath) in a compressed configuration to deliver the thin-film neural interfaces to a target biological structure. Alternatively, a medical device is obtained comprising the self-expanding stent including one or more thin-film neural interfaces predisposed within a delivery device (e.g., a delivery sheath) in a compressed configuration to deliver the thin-film neural interface to a target biological structure. The delivery device is configured to compress a top portion of the stent, which allows efficient delivery of the thin-film neural interface regardless of the orientation of the stent. In addition, use of the delivery device can prevent engagement/interfacing of the thin-film neural interface with tissue or bodily fluid until the delivery device is removed or the stent is deployed from the delivery device. The delivery device may comprise a removable material (e.g., peelable or absorbable material) that surrounds or covers at least the thin-film neural interface and the stent. In some instances, the delivery device is made from one or more of an implantable grade resorbable or non-resorbable polymer and/or metal material. In certain instances, the delivery device comprises one or more of polypropylene, polyester, nylon, polyether ether ketone (PEEK), polyurethane, polycarbonate, titanium, and stainless steel.

At optional step 710, one or more incisions are made in a subject (e.g., a patient) to access a target biological structure. At step 715, the medical device is inserted and/or guided into a cavity of a body (optionally through the one or more incisions) to a target site of the biological system. In some embodiments, the cable portion of the thin-film lead assembly comprises a lumen that extends from a proximal end of the thin-film lead assembly through the stent to a distal end of the thin-film lead assembly. The lumen may have a diameter wide enough to receive a guide wire for guiding the thin-film lead assembly to a target site of the biological system.

At step 720, once the medical device reaches the target site of the biological system, the delivery device is retracted from at least the thin-film neural interface, and the stent is used to deploy the thin-film neural interface. Once the thin-film neural interface is at a target location, the delivery device is removed from the distal end of the thin-film lead assembly and the guide wire is removed from the lumen. Thereafter, the thin-film neural interface is deployed using the stent. The deploying comprises expanding the stent from the compressed configuration (FIG. 4A) to an expanded configuration (FIG. 5A) that places the electrodes into contact with the target biological structure (e.g., a blood vessel wall).

In some embodiments, the stent is deployed and expands automatically once the delivery device is retracted from the stent (e.g., once the compression force provided by the delivery device is removed, the stent automatically expands (for example, memory shape expansion)). In some instances, the stent is deployed in a blood vessel and the stent allows blood flow that is uninterrupted through the blood vessel. Advantageously, the stent allows for the thin-film neural interface to intimately contact the blood vessel wall. Moreover, the thin-film neural interface can support a dense arrangement electrodes for interfacing consistently with the target biological structure.

With reference back to FIG. 7, at step 725, the thin-film lead assembly is connected to a computing device (e.g., a pulse generator or an interfacing processor). As described with respect to FIG. 1, the computing device can be implantable, semi-implantable, or an external system. At step 730, the neural interface is used to provide neurostimulation and/or sense electrical activity at the target biological structure.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. A medical device comprising:
 a stent comprising:
  a plurality of struts arranged in series from a proximal end to a distal end of the stent, wherein each strut of the plurality of struts comprises: a top portion, a base portion integrally connected with the top portion at a first connection point and a second connection point, a first hinge disposed at the first connection point, and a second hinge disposed at the second connection point, wherein the first hinge and the second hinge allow the top portion to move at an angle from −30° to 90° relative to the base portion;
  a first cross-bar attached to the first connection point of each strut of the plurality of struts;
  a second cross-bar attached to the second connection point of each strut of the plurality of struts; and
  a third cross-bar attached to the top portion of each strut of the plurality of struts; and
 a thin-film neural interface comprising:
  a supporting structure having a first surface and a second surface opposite of the first surface; and
  one or more electrodes formed on the first surface of the supporting structure, wherein the second surface of the supporting structure is attached to the base portion of each strut of the plurality of struts.

2. The medical device of claim 1, wherein each strut of the plurality of struts have an elliptical or circular geometry.

3. The medical device of claim 2, wherein the base portion of each strut of the plurality of struts is an arc that is less than one half of a circumference of the elliptical or circular geometry, and wherein the top portion of each strut of the plurality of struts is an arc that is greater than one half of a circumference of the elliptical or circular geometry.

4. The medical device of claim 3, wherein the stent comprises stainless steel, Nitinol, nickel, titanium, or any combinations thereof.

5. The medical device of claim 1, wherein the stent is a monolithic structure.

6. The medical device of claim 1, wherein each strut of the plurality of struts is spaced a predetermined distance from adjacent struts of the plurality of struts.

7. The medical device of claim 6, wherein the predetermined distance is at least 0.5 mm.

8. The medical device of claim 1, wherein the thin-film neural interface further comprises a wiring layer formed on the supporting structure, and the one or more electrodes are electrically connected to the wiring layer, and wherein the supporting structure comprises one or more layers of dielectric material.

9. The medical device of claim 8, wherein the dielectric material is liquid crystal polymer.

10. The medical device of claim 8, further comprising:
a cable comprising:
the supporting structure comprised of the dielectric material;
one or more conductive traces formed on the supporting structure and electrically connected with the wiring layer; and
one or more encapsulation layers encasing at least a portion of the supporting structure.

11. The medical device of claim 10, wherein the cable further comprises a proximal end and a distal end, and the thin-film neural interface is disposed at the distal end of the cable.

12. The medical device of claim 11, further comprising:
a connector disposed at the proximal end of the cable and electrically connected to the one or more conductive traces; and
a neurostimulator or computing device electrically connected with the one or more electrodes via the connector, the one or more conductive traces, and the wiring layer.

13. The medical device of claim 1, wherein the second surface of the supporting structure is attached to the base portion of each strut of the plurality of struts via an adhesive.

* * * * *